United States Patent [19]

Legendre et al.

[11] Patent Number: 5,759,827
[45] Date of Patent: Jun. 2, 1998

[54] ACYLATED OLIGOPEPTIDES FOR TRANSFECTING CELLS

[75] Inventors: Jean-Yves Legendre, Paris, France; Andreas Supersaxo, Basel, Switzerland; Arnold Trzeciak, Schopfheim, Germany

[73] Assignee: Hoffmann-La Roche Inc., Nutley, N.J.

[21] Appl. No.: 752,129

[22] Filed: Nov. 20, 1996

[30] Foreign Application Priority Data

Nov. 22, 1995 [EP] European Pat. Off. ............. 95118338

[51] Int. Cl.$^6$ ............................................. C12N 15/00
[52] U.S. Cl. ................... 435/172.1; 435/172.3; 435/244; 514/2; 935/33; 935/34; 935/52; 935/54
[58] Field of Search .................. 424/450; 514/12–19, 514/2; 435/172.1, 172.3, 244; 935/33, 34, 52, 54

[56] References Cited

FOREIGN PATENT DOCUMENTS 0727223  8/1996  European Pat. Off. .

OTHER PUBLICATIONS

Helv. Chim. Acta, pp. 526–543, (See pp. 543–544 for English language summary) (1964).

Felgner, et al, Lipofection: A highly efficient, lipid–mediated DNA–transfection procedure, Proc. Natl. Acad. Sci. vol. 84, pp. 7413–7417 (1987).

Behr, Gene Transfer with Synthetic Cationic Amphiphiles: Prospects for Gene Therapy, Bioconjugate Chem., vol. 5, pp. 382–389 (1994).

Gao, et al. Cationic liposome–mediated gene transfer, Gene Therapy, vol. 2, pp. 710–722 (1995).

Kabanov, et al. DNA Complexes with Polycations for the Delivery of Genetic Material into Cells, Bioconjugate Chem., vol. 6, pp. 7–20 (1995).

Ledley, Nonviral Gene Therapy: The Promise of Genes as Pharmaceutical Products, Human Gene Therapy, vol. 6, pp. 1129–1144 (1995).

Kabanov et al. "DNA Complexes with Polycations for the Delivery of Genetic Material into Cells", *Bioconjugate Chemistry*, vol. 6, No. 1(1995), pp. 7–20. QP517.B49B56.

Lee et al. "Folate–Targeted, Anionic Liposome–Entrapped Polylysine–Condensed DNA for Tumor Cell–Specific Gene Transfer", *Journal of Biological Chemistry*, vol. 271, No. 14 (Apr. 5, 1996), pp. 8481–8487. QP501.J7.

Volger et al. "Ferrsäurehaltige basiche Peptide mit Antibakterieller Wirkung", *Helvetica Chimic Acta*, vol. 47 (1964), pp. 526–543. QD1.H4.

Primary Examiner—Laurie Scheiner
Assistant Examiner—Jeffrey Stucker
Attorney, Agent, or Firm—George W. Johnston; William H. Epstein; Briana C. Buchholz

[57] ABSTRACT

Compounds of the formula

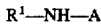

I wherein $R^1$ is an acyl moiety of a $C_{12-40}$ aliphatic carboxylic acid, A is the residue of a oligopeptide devoid of one amino group, and —NH—A contains at least one positively charged amino acid, or derivatives thereof can be used for transferring anionic macromolecules into cells.

24 Claims, No Drawings

ACYLATED OLIGOPEPTIDES FOR TRANSFECTING CELLS

BACKGROUND OF THE INVENTION

Gene transfer technology has become a field of considerable interest. Introduction of an exogeneous gene into a cell (i.e. transfection) bears many important scientific and medical applications, going from gene regulation and the production of recombinant proteins to gene therapy.

Viruses have evolved to bypass the different cellular barriers to gene transfer and have indeed become vectors of choice for transfection. Many viruses, including retrovirus, adenovirus or herpes virus, are now engineered to carry therapeutic genes and used in human clinical trials for gene therapy. However, there remains a risk of infectious and immunologic reaction and the large scale production of viruses is difficult and time consuming.

For these various reasons non viral systems have been developed to carry DNA into cells, e.g., the transfection technique based on a cationic lipid, the dioleoyloxy trimethylammonium (Felgner et al., Proc. Natl., Acad. Sci. U.S.A., 84, 7413–7417, 1987) commercialized as Lipofectin™. Since the discovery of this transfection technique, many more cationic lipids have been synthezised and some are commercially available as transfecting reagent for laboratory use: DOGS (Transfectam™), DOSPA (Lipofectamine™), DOTAP (DOTAP™).

Nevertheless, despite important progress in the formulation of non-viral gene delivery systems, there remains a need for more efficient techniques, since the transfection efficiency of synthetic systems is usually below that of viral vectors. Furthermore, many problems still arise in vivo and the poor stability of the non-viral systems in biological fluids does not allow high and reproducible levels of transfection in vivo.

SUMMARY OF THE INVENTION

This invention provides a method of transfecting a cell with an anionic macromolecule, comprising contacting the cell with the anionic macromolecule in the presence of a compound of the formula $$R^1-NH-A \quad \quad I$$

wherein $R^1$ is an aliphatic acyl moiety of about 12 to about 40 carbon atoms; and —NH—A is an oligopeptide or a derivative thereof, wherein —NH—A contains at least one positively charged amino acid, so as to transfect the cell with the anionic macromolecule.

This invention provides a method of transfecting a cell with an anionic macromolecule containing at least one negative charge per molecule, comprising contacting the cell with a composition, wherein the composition comprises at least one compound of formula I, wherein $R^1$ is an aliphatic acyl moiety of 12 to 40 carbon atoms, an —NH—A is an oligopeptide or a derivative thereof, wherein —NH—A contains at least one positively charged amino acid; and from 0.1 nanogram to 1 gram of an anionic macromolecule, where in the compound is present in an amount sufficient to provide a positive to negative charge ratio from 0.1 to 10 in the composition.

This invention provides a composition comprising at least one compound of formula I where $R^1$ is an aliphatic acyl moiety of about 12 to 40 carbon atoms, and —NH—A is an oligopeptide or a derivative thereof, wherein —NH—A contains at least one positively charged amino acid; and from 0.1 ng to 1 g of an anionic macromolecule containing at least one negative charge per molecule, wherein the compound is present in an amount sufficient to provide a positive to negative charge ratio from 0.1 to 10 in the composition.

This invention also provides a composition adapted to deliver from 0.1 ng to 1 g of an anionic macromolecule containing at least one negative charge per molecule, comprising a compound of formula I, wherein $R^1$ is an aliphatic acyl moiety of about 12 to about 40 carbon atoms, and —NH—A is an oligopeptide or a derivative thereof, wherein —NH—A contains at least one positively charged amino acid, wherein the compound is present in an amount sufficient to provide a positive to negative charge ratio from 0.1 to 10 when mixed with the anionic macromolecule; and a helper lipid or a short chain phospholipid.

In accordance with the present invention it has been found that oligopeptides coupled to a fatty acid moiety can bind nucleic acids and can be used for transfection of cells.

DETAILED DESCRIPTION OF THE INVENTION

In one aspect, the present invention relates to the use of a compound of the formula $$R^1-NH-A \quad \quad I$$

wherein $R^1$ is an acyl moiety of a $C_{12-40}$ aliphatic carboxylic acid and A is the residue of an oligopeptide devoid of one amino group, or a derivative thereof, as a carrier for transfecting a cell with an anionic macromolecule.

Transfection of cells with oligonucleotides such as DNA can be used, for example to express in a host cell or organism, a protein which is not normally expressed by that cell or organism. For example, a self replicating DNA molecule called a plasmid may be introduced into a cell not normally containing that plasmid in order to express a marker gene product in that cell, or to express a protein of interest such as a recombinant protein which is later harvested from such cells. (See Sambrook, et al., Molecular Cloning: A Laboratory Manual, 2nd ed. (Cold Spring Harbor, 1989), ch. 1.) The transfection of oligonucleotides into cells can also be used therapeutically. For example, antisense oligonucleotides, once in the cell or cell nucleus, bind to target single-stranded nucleic acid molecules by Watson-Crick base pairing or to double stranded nucleic acids by Hoogsteen base pairing, and in doing so disrupt the function of the target by one of several mechanisms: by preventing the binding of factors required for normal transcription, splicing, or translation; by triggering the enzymatic degradation of mRNA by RNAse H, or by destroying the target via reactive groups attached directly to the antisense oligonucleotide. (See Zamecnic et al., Proc. Natl. Acad. Sci.-U.S.A. (1978) 75: 280–284).

Proteins and other anionic macromolecules are transferred into cells for therapeutic and screening purposes. For example, immunization is enhanced by introducing an immunogenic protein into a cell, so that it is more efficiently processed and presented on the surface of the cells, thereby enhancing the immunogenic response. Negatively charged anionic macromolecules which act inside a cell are transported past the hydrophobic cell membrane into the cytoplasm where they exert their effect. Factors which enhance or hinder transcription of DNA can be used in a screening test to verify the transcription of a gene of interest. These transcription assays are very well known for use in screening compounds to determine their effect against a particular macromolecule, for example a cell receptor.

The term "$C_{12-40}$" denotes a number of carbon atoms of from 12 to 40. The acyl moiety $R^1$ can be a straight-chain or branched chain, saturated or unsaturated moiety. Preferably, the acyl moiety $R^1$ contains from 12 to 20 carbon atoms. Examples of such moieties are lauroyl, palmitoyl, stearoyl, oleoyl, and $(CH_3(CH_2)_n)_2CHCO-$, where n is an integer from 3 to 19. Most preferred are palmitoyl and oleoyl.

The term "oligopeptide" refers to peptides containing up to 20, preferably up to 10, more preferably from 2 to 6 amino acids residues containing at least one basic amino acid. The term "basic amino acid" denotes an amino acid which, because it contains more basic groups (such as amino, amidino or guanidino) than carboxylic groups, is positively charged. Examples of such basic amino acids are natural and unnatural diamino-monocarboxylic acids, such as $\alpha,\beta$-diaminopropionic acid, $\alpha,\gamma$-diaminobutyric acid, lysine, arginine, ornithine and p-aminophenylalanine. The amino acids may belong to the L-or D-series or may be racemic. $\alpha,\gamma$-diaminobutyric acid, lysine and ornithine are preferred amino acid constituents of the compounds of formula I.

In practicing the invention, the cell is contacted with the anionic macromolecule in the presence of an appropriate amount of a compound of formula I. The appropriate amount of the compound of formula I for a given amount of anionic macromolecule depends on their respective charges. The +/− charge ratio between compound I and the molecule to be transfected generally varies between 0.1–10, preferably between 0.5–5. The value of "+/− charge ratio" is calculated by dividing the number of positively charged groups on the amino acids in the group "A" by the number of negative charges of the molecule to be transfected. When the molecule to be transfected is a polynucleotide for example, number of negative charges means the number of negatively charged phosphates in the backbone. The optimal ratio within these ranges depends on the cell to be transfected and is readily ascertained by one of skill in the art to which this invention pertains.

The amount of anionic macromolecules to the number of cells is such that the amount of anionic macromolecule for transfecting $10^4$ cells is from 0.1 ng to 10 μg, preferably from 0.2 μg to 2 μg. When the anionic macromolecule is DNA the preferred amount of DNA for transfecting $10^4$ cells in vitro is from 0.1 μg to 10 μg. When cells are being transfected in vivo, the preferred amount of DNA is from 0.1 μg to 1 g.

The term "derivatives" refers to oligopeptides wherein the terminal carboxyl group is esterified, particularly to form lower alkyl esters such as the methyl and ethyl ester; or converted into an amide, lower alkyl amide or di-lower alkyl amide or hydrazide. Hydrazides are the preferred derivatives. The term "lower" denotes groups containing from 1–6 carbon atoms.

In accordance with this invention, any anionic macromolecule can be transfected into a cell using a compound of formula I. An anionic macromolecule is a macromolecule which contains at least one negative charge per molecule. Examples of anionic macromolecules which can be transfected in accordance with this invention include polynucleotides, such as deoxyribonucleic acids (DNA) and ribonucleic acids (RNA); and proteins, such as ribonucleoproteins and proteins used for immunization, e.g. viral proteins. Examples of DNA for use in the present invention are plasmids and genes, especially those for which gene therapy protocols have been launched such as cystic fibrosis transmembrane regulator (CFTR), adenosine deaminase (ADA), thymidine kinase (tk) and HLA B7; as well as reporter genes such as beta-galactosidase, luciferase, chloramphenicol transferase and alpha-1 antitrypsin. Other examples of DNA are oligodeoxynucleotides and their analogues used as antisense, aptamer or "triple-helix" agents. Examples of RNA are ribozymes or oligoribonucleotide antisense molecules.

Examples of compounds of formula I for use in the present invention are Nα-palmitoyl-L-lysyl-L-lysine and the methyl and ethyl ester thereof; Nγ-palmitoyl-D-($\alpha,\gamma$-diaminobutyryl)-L-($\alpha,\gamma$-diaminobutyric acid) hydrazide; and Nγ-palmitoyl-D-($\alpha,\gamma$-diaminobutyryl)-D-($\alpha,\gamma$-diaminobutyryl)-L-($\alpha,\gamma$diaminobutyric acid)hydrazide. Compounds of formula I are known, see Helv. Chim. Acta 47 (1964) p. 526–543.

The nature of the cell which is to be transfected is not narrowly crucial. The cell can be a procaryotic or eucaryotic cell, a mammalian or a plant cell.

In a preferred aspect of the invention the transfection is further carried out in the presence of a helper lipid and/or short chain phospholipid and/or a known transfection competent molecule other than a compound of formula I. Any conventional helper lipid can be used in carrying out this invention. Helper lipids are phospholipids which are known to increase delivery of macromolecules to cells when used together with known transfection competent molecules. Examples of helper lipids are phospholipids, such as phosphatidylcholine or phosphatidylethanolamines or mixtures thereof. Preferred helper lipids are phosphatidylethanolamines, such as dioleoylphosphatidylethanolamine. Any conventional short chain phospholipid can be used in carrying out this invention. Short chain phospholipids are phospholipids containing fatty acid residues, which fatty acid residues contain from 6 to 12 carbon atoms in their backbone. Examples of short chain phospholipids are phosphatidylcholines that carry two $C_{6-12}$ fatty acid residues. Preferred short chain phospholipids are dicapryl- and dicapryloyl phosphatidylcholine. The helper lipid and/or short chain phospholipid is suitably in the form of a liposome, micelles, organic or aqueous dispersions, or organic or aqueous solutions. The optimal molar ratio between the compound of formula I and the helper lipid is 0.1–50, preferably 1–10. The optimal molar ratio between helper lipid and short-chain phospholipid is 2–20.

When a transfection competent molecule in addition to the compound of formula I is used, any conventional transfection competent molecule can be used in carrying out this invention. Transfection competent molecules are molecules which are capable of enhancing the transfection of cells in solutions which contain the molecule to be transfected, the cell, and the transfection molecule. Examples of transfection competent molecules include cationic lipids as described by J. B. Behr in Bioconjugate Chem. 5:382–389 (1994) and X. Gao and L. Huang in Gene Ther. 2:710–722 (1995); polycations as described by A. V. Kabanov and V. A.: Kabanov in Bioconjugate Chem. 6:7–20 (1995); peptides and polymers and other nonviral gene delivery systems as described by F. D. Ledley in Human Gene Therapy 6:1129–1144 (1995). The optimal molar ratio between the compound of formula 1 and other transfection competent molecules is 0.1–10.

In another aspect, the invention is concerned with a composition comprising a compound of formula I as defined above, a polynucleotide or any other anionic macromolecule, and optionally, a helper lipid and/or a short chain phospholipid and/or a known transfection competent molecule other than the compound of formula I. In still another aspect the invention is concerned with a composition comprising a compound of formula I as defined above, and a helper lipid and/or a short chain phospholipid, and/or a known transfection competent molecule other than the compound of formula I. In accordance with this invention the composition contains an amount of the compound of formula I, and optionally one or more of a helper lipid, a short chain phospholipid, and a known transfection competent molecule other than a compound of formula I, to deliver from 0.1 ng to 1 g of the anionic macromolecule, for example DNA. For transfecting cells in vitro the composition is preferably adapted to deliver from 0.1 µg to 10 µg to target $10^4$ cells. For delivering DNA in vivo the composition is preferably adapted to deliver from 0.1 µg to 1 g DNA. Optimal ratios of the various components are described above.

In practicing the invention, an appropriate amount of a compound of formula I is added to the molecule to be transfected (e.g., plasmid DNA), suitably in an aqueous solution. The amounts of the compound of formula I and the ánionic macromolecule should be chosen so as to produce a +/− charge ratio in the composition of between 0.1–10, preferably between 0.5–5. A helper lipid and, if desired, a short chain phospholipid and/or a known transfection competent molecule other than the compound of formula I is then added, either in form of liposomes, micelles, organic or aqueous dispersions, or organic or aqueous solutions. Alternatively, the molecule to be transfected may be added to a composition comprising a compound of formula I, a helper lipid, and, if desired, a short chain phospholipid and/or an other known transfection competent molecule. The composition may be in solid, liquid, semisolid or aerosol form, suitably in the form of liposomes, micelles, organic or aqueous dispersions, or organic or aqueous solutions.

For transfection, the composition comprising a compound of formula I as defined above, a polynucleotide or any other anionic macromolecule, and, optionally, a helper lipid and/or a short-chain phospholipid and/or an other known transfection competent molecule as defined above is added to the cells. For transfecting cells in an animal or human patient the composition can be administered by oral, parenteral (i.v., i.m., s.c., i.d., i.p.) transdermal, pulmonary, nasal, rectal, ocular, ventricular, vascular (catheter) and intratumoral route. Furthermore, the composition can be administered by high velocity impaction administration to the skin surface. The progress of transfection can be measured by appropriate testing protocols which are known to those skilled in the art.

The following examples which are not limitative illustrate the invention which is defined in the claims which follow.

Example 1

Dioleoyl phosphatidylethanolamine (DOPE, Avanti Polar Lipids Inc.) liposomes were prepared by drying under vacuum the lipid in solution in chloroform and then rehydrating the lipid film with 30 mM Tris Cl pH 8.5. Final lipid concentration was 2 mM. The lipid dispersion was subsequently sonicated for 10–15 min in a sonicator bath (Elgasonic, 50 kHz).

Twenty µg of plasmid DNA were diluted with 260 µl of distilled, sterile water in a polystyrene sterile tube. Then, 56 nmoles (35.2 µg) of Nγ-palmitoyl-D-(α,γ-diaminobutyryl)-L-(α,γ-diaminobutyric acid) hydrazide were added so that the +/− charge ratio between Nγ-palmitoyl-D-(α,γ-diaminobutyryl)-L-(α,γ-diaminobutyric acid) hydrazide and the DNA was 2:1. 140 µl of DOPE liposomes were then slowly added, drop by drop, to obtain a molar ratio between DOPE and Nγ-palmitoyl-D-(α,γ-diaminobutyryl)-L-(α,γ-diaminobutyric acid) hydrazide of 5:1. The complex was carefully mixed. The preparation was allowed to stand at room temperature during about 5 min and was then added to COS-1 cells grown in 96-well plates.

A similar procedure of preparation was used for the other compounds of formula I.

The transfection efficiency of the various compounds is shown Table 1.

TABLE 1

Transfection efficiency of compounds of formula I formulated as in example 1 of COS-1 cells.
Cells were transfected with a beta-galactosidase encoding plasmid and beta-galactosidase activity was measured 48 h after transfection. Results are expressed as µunits of beta-galactosidase per trasfection well.

| Compound of formula I | Beta-galactosidase activity 0.2 µg DNA/well | 1 µg DNA/well |
|---|---|---|
| $N^\gamma$ palmitoyl-D (α,γ-diaminobutyryl)-L (α,γ-diaminobutyric acid) hydrazide | 5772 | 9942 |
| $N^\alpha$ palmitoyl-L (α,γ-diaminobutyryl)-L (α,γ-diaminobutyric acid) hydrazide | 2742 | 3519 |
| $N^\gamma$ palmitoyl-D (α,γ-diaminobutyryl)-D (α,γ-diaminobutyryl)-L (α,γ-diaminobutyric acid) hydrazide | 1847 | 7768 |
| $N^\gamma$ palmitoyl-L (α,γ-diaminobutyryl)-D (α,γ-diaminobutyryl)-D (α,γ-diaminobutyryl)-L (α,γ-diaminobutyric acid) hyrazide | 497 | 542 |
| $N^\gamma$ palmitoyl-L (α,γ-diaminobutyryl)-L (α,γ-diaminobutyryl)-L (α,γ-diaminobutyryl)-L (α,γ-diaminobutyric acid) hydrazide | 1800 | 7835 |
| $N^\alpha$ palmitoyl-L (α,γ-diaminobutyric acid) hydrazide | 606 | 1411 |
| $N^\gamma$ γ palmitoyl-D (α,ε-diaminopropionyl)-L (α,ε-diaminopropionic acid) hydrazide | 0 | 3671 |
| $N^\gamma$ palmitoyl-D (α,ε-diaminopropionyl)-L (α,ε-diaminopropionic acid) ethyl ester | 359 | 0 |
| $N^\alpha$ palmitoyl-L lysyl-L lysine ethyl ester | 138 | 424 |
| $N^\alpha$ palmitoyl-L lysyl-L lysyl-L lysine hydrazide | 136 | 2232 |
| $N^\alpha$ palmitoyl-L lysyl-L lysine methyl ester | 0 | 150 |
| $N^\alpha$ palmitoyl-L lysyl-L lysine | 0 | 530 |
| $N^\epsilon$ palmitoyl-L lysyl-L lysine methyl ester | 0 | 100 |
| $N^\epsilon$ palmitoyl-L lysyl-L lysyl-L lysine methyl ester | 0 | 1426 |
| $N^\alpha$ oleoyl-L lysyl-L lysine ethyl ester | 0 | 1333 |
| $N^\alpha$ methyl arachidoyl-L lysyl-L lysine methyl ester | 0 | 148 |
| $N^\alpha$ palmitoyl-L arginyl-L arginine ethyl ester | 0 | 382 |
| $N^\alpha$ palmitoyl-L ornithyl-L ornithine methyl ester | 44 | 789 |
| $N^\alpha$ palmitoyl-(L ornithyl)$_5$-L ornithine ethyl ester | 625 | 12210 |
| $N^\alpha$ palmitoyl-L lysyl-L serine methyl ester | 0 | 219 |
| $N^\alpha$ palmitoyl-L arginyl-L ornithine methyl ester | 0 | 870 |
| $N^\alpha$ palmitoyl-L (α,γ-diaminobutyryl)-L lysine methyl ester | 62 | 791 |
| $N^\alpha$ palmitoyl-L lysyl-L lysine benzylamide | 510 | 845 |

Example 2

Mixed micelles of DOPE (2 µmoles) and dicaproyl phosphatidylcholine (15 µmotes) were prepared by drying the lipids under vacuum and then rehydrating the lipid film with 1 ml of 30 mM TrisCl buffer pH 8.5. Twenty µg of plasmid pCH110 were diluted with 260 µl of distilled water in a polystyrene sterile tube. Then, 56 nmoles (35.2 µg) of Nµ-palmitoyl-D-(α,γ-diaminobutyryl)-L-(α,γ-diaminobutyric acid) hydrazide was added so that the +/− charge ratio between Nγ-palmitoyl-D-(α,γ-diaminobutyryl)-L-(α,γ-diaminobutyric acid) hydrazide and the DNA was 2:1. 140 µl of DOPE/dicyproyl PC mixed micelles were then slowly added to obtain a molar ratio between DOPE and Nγ-palmitoyl-D-(α,γ-diaminobutyryl)-L-(α,γ- diaminobutyric acid) hydrazide of 5:1. The complex was carefully mixed. The preparation was allowed to stand at room temperature during about 5 min and was then added to COS-1 cells grown in 96-well plates.

The transfection efficiency of COS-1 cells, expressed as beta-galactosidase activity, was 7280 and 6375 µUnits per well for 0.2 µg and 1 µg of DNA per well, respectively.

Example 3

56 nmoles (35.2 µg) of Nγ-palmitoyl-D-(α,γ-diaminobutyryl)-L-(α,γ-diaminobutyric acid) hydrazide was mixed with a 5 molar excess of DOPE liposomes (280 nmoles), prepared as in example 1. The mixture was added to 20 µg of plasmid DNA in 260 µl of distilled water, so that the +/− charge ratio between Nγ-palmitoyl-D-(α,γ-diaminobutyryl)-L-(α,γ-diaminobutyric acid) hydrazide and plasmid DNA was 2:1. The complex was carefully mixed. The preparation was allowed to stand at room temperature during about 5 min and was then added to COS-1 cells grown in 96-well plates.

The transfection efficiency of COS-1 cells, expressed as beta-galactosidase activity, was 4205 and 7880 µUnits per well for 0.2 µg and 1 µg of DNA per well, respectively.

Example 4

A transfecting complex with Nγ-palmitoyl-D-(α,γ-diaminobutyryl)-L-(α,γ-diaminobutyric acid) hydrazide (compound A) was prepared as described in example 1. Lipofectamine™ complex was prepared following manufacturer's instructions. The transfection efficiency of both systems was compared in various cell-lines using a luciferase encoding vector.

Results are given in Table 2.

TABLE 2

| Cell-line | cpd A | Lipofectamine | enhancement cpd A over Lipofectamine |
| --- | --- | --- | --- |
| 293-EBNA | 5.0 10⁵ | 9.9 10⁴ | 5 |
| CHO K1 | 1.6 10⁶ | 4.8 10⁴ | 33 |
| HeLa | 1.0 10³ | 2.4 10² | 4 |
| LM tk- | 5.7 10⁵ | 4.5 10⁴ | 12 |

Cells were transfected with a luciferase encoding plasmid and luciferase activity was measured 48 h after transfection. Results are expressed as relative light units.

What is claimed is:

1. A method of transfecting a cell with an anionic macromolecule containing at least one negative charge per molecule, comprising contacting the cell with the anionic macromolecule in the presence of a compound of the formula $$R^1-NH-A \qquad I$$

wherein $R^1$ is an aliphatic moiety of 12 to 40 carbon atoms; and —NH—A is a positively charged oligopeptide or a positively charged derivative thereof, so as to transfect the cell with the anionic macromolecule.

2. The method of claim 1 wherein the oligopeptide contains from 2 to 10 amino acid residues.

3. The method of claim 2 wherein the oligopeptide contains from 2 to 6 amino acid residues.

4. The method of claim 1 wherein the ratio of the positive charge on the compound to the negative charge on the anionic macromolecule is between 0.1 and 10.

5. The method of claim 3 wherein the oligopeptide contains at least one α,γ-diaminobutyric acid residue, ornithine residue or lysine residue.

6. The method of claim 1 wherein the derivative is an oligopeptide containing a carboxy-terminal hydrazide.

7. The method of claim 1 wherein $R^1$ is palmitoyl or oleoyl.

8. The method of claim 1 further comprising wherein the contacting is in the presence of at least one transfection competent molecule in addition to the compound of formula I.

9. The method of claim 1 further comprising wherein the contacting is in the presence of a helper lipid in addition to the compound of formula I.

10. The method of claim 9 wherein the helper lipid comprises a phosphatidylcholine or a phosphatidylethanolamine.

11. The method of claim 10 wherein the phosphatidylethanolamine is dioleoylphosphatidylethanolamine.

12. The method of claim 1 further comprising wherein the contacting is in the presence of a short chain phospholipid in addition to the compound of formula I.

13. The method of claim 12 wherein the short chain phospholipid is dicaprylphosphatidylcholine or dicapryloyl phosphatidylcholine.

14. The method of claim 1, wherein the anionic macromolecule is a polynucleotide.

15. The method of claim 1 further comprising wherein the contacting is in the presence of a helper lipid and a transfection competent molecule.

16. A method of transfecting at least one cell to about 10₄ cells in vitro with an anionic macromolecule containing at least one negative charge per molecule, comprising contacting the cell with a composition, wherein the composition comprises:

at least one compound of the formula $$R^1-NH-A \qquad I$$

wherein $R_1$ is an aliphatic acyl moiety of 12 to 40 carbon atoms, and
—NH—A is a positively charged oligopeptide or a positively charged derivative thereof; and from 0.1 nanogram to 10 µg of an anionic macromolecule wherein the compound is present in an amount sufficient to provide to negative charge ratio from 0.1 to 10 in the composition.

17. A composition comprising at least one compound of the formula $$R^1-NH-A \qquad I$$

wherein $R^1$ is an aliphatic acyl moiety of 12 to 40 carbon atoms, and
—NH—A is a positively charged oligopeptide or a positively charged derivative thereof; and from 0.1 nanogram to 1 gram of an anionic macromolecule containing at least one negative charge per molecule.

18. The composition of claim 17, wherein the anionic macromolecule is a polynucleotide.

19. The composition of claim 17, further comprising a helper lipid and/or a short chain phospholipid and/or a known transfection competent molecule other than the compound of formula I.

20. A composition adapted to deliver to a living organism from 0.1 microgram to 1 gram of an anionic macromolecule containing at least one negative charge per molecule, comprising a compound of the formula

R¹—NH—A          I wherein R¹ is an aliphatic acyl moiety of 12 to 40 carbon atoms, and —NH—A is a positively charged oligopeptide or a positively charged derivative thereof, wherein the compound is present in an amount sufficient to provide a positive to negative charge ratio from 0.1 to 10 when mixed with the anionic macromolecule; and a helper lipid and/or a short chain phospholipid and/or a transfection competent molecule other than the compound of formula I.

21. The composition of claim 20, wherein the helper lipid is a phosphatidylcholine or a phosphatidylethanolamine.

22. The composition of claim 20 wherein the helper lipid or short chain phospholipid is in the form of liposomes, micelles, organic or aqueous dispersions, or organic or aqueous solutions.

23. The composition of claim 20 wherein the composition is in solid, liquid, semisolid or aerosol form.

24. A method of transfecting a cell in vivo with an anionic macromolecule containing at least one negative charge per molecule, comprising contacting the cell with a composition, wherein the composition comprises:

at least one compound of the formula

R¹—NH—A          I wherein R¹ is an aliphatic acyl moiety of 12 to 40 carbon atoms, and —NH—A is a positively charged oligopeptide or a positively charged derivative thereof, and from 0.1 microgram to 1 gram of the anionic macromolecule, wherein the compound is present in an amount sufficient to provide a positive to negative charge ratio from 0.1 to 10 in the composition.

\* \* \* \* \*